United States Patent
LaFlech

(10) Patent No.: US 10,701,270 B1
(45) Date of Patent: Jun. 30, 2020

(54) CAMERA DISPLAY WELDER'S HELMET

(71) Applicant: Thomas J. LaFlech, Lowell, IN (US)

(72) Inventor: Thomas J. LaFlech, Lowell, IN (US)

( * ) Notice: Subject to any disclaimer, the term of this patent is extended or adjusted under 35 U.S.C. 154(b) by 886 days.

(21) Appl. No.: 14/563,410

(22) Filed: Dec. 8, 2014

Related U.S. Application Data

(60) Provisional application No. 61/993,476, filed on May 15, 2014.

(51) Int. Cl.
| | | |
|---|---|---|
| *A61F 9/06* | (2006.01) | |
| *H04N 5/232* | (2006.01) | |
| *H04N 5/225* | (2006.01) | |

(52) U.S. Cl.
CPC .......... *H04N 5/23293* (2013.01); *A61F 9/06* (2013.01); *H04N 5/2252* (2013.01)

(58) Field of Classification Search
CPC .................................................. H04N 5/23293
USPC ........................................................... 348/82
See application file for complete search history.

(56) References Cited

U.S. PATENT DOCUMENTS

| | | | |
|---|---|---|---|
| 4,621,283 A | 11/1986 | Feinbloom | |
| 5,857,215 A * | 1/1999 | Fergason | ............... A61F 9/06 2/412 |
| 6,230,327 B1 * | 5/2001 | Briand | ............... A61F 9/06 2/8.1 |
| 6,668,134 B1 | 12/2003 | Niikawa | |
| 6,734,393 B1 * | 5/2004 | Friedl | ............... A61F 9/067 219/130.01 |
| 8,502,866 B2 | 8/2013 | Becker et al. | |
| 2001/0049837 A1 | 12/2001 | Slack | |
| 2010/0223706 A1 * | 9/2010 | Becker | ............... A42B 3/30 2/8.2 |
| 2011/0083241 A1 * | 4/2011 | Cole | ............... A61F 9/06 2/8.2 |
| 2012/0291172 A1 * | 11/2012 | Wills | ............... B23K 9/0956 2/8.2 |

(Continued)

FOREIGN PATENT DOCUMENTS

| | | | |
|---|---|---|---|
| WO | 2005102230 A1 | 11/2005 | |
| WO | WO 2005102230 A1 * | 11/2005 | ............... A61F 9/06 |

OTHER PUBLICATIONS

Hillers B, Aiteanu D, Tschirner P, Park M, Graser A, Balazs B, Schmidt L. TEREBES: welding helmet with AR capabilities. International Status Conference: Virtual and Augmented Reality, Leipzig, Germany 2004.*

*Primary Examiner* — Ayman A Abaza
(74) *Attorney, Agent, or Firm* — Cramer Patent & Design, PLLC; Aaron R. Cramer

(57) ABSTRACT

A light blocking welding helmet having a helmet body with a shell having a head aperture produces an image from at least one (1) exterior camera within the helmet body. The helmet body includes an interior cavity containing an adjustable headband and an internal power source for powering the viewing screen and camera. The camera is mounted on the helmet body. Electrical circuitry is operatively connected to the power source, to the viewing screen, and to the camera such that the electrical circuitry causes the viewing screen to display the image produced by the camera. The image can be transmitted to a remote receiving unit where a weld can be monitored. Multiple cameras may be used and a control switch then selects which camera that will produce an image.

20 Claims, 4 Drawing Sheets

(56) References Cited

U.S. PATENT DOCUMENTS

2015/0026872 A1* 1/2015 Giroux Bernier ....... A42B 1/24
2/422

* cited by examiner

CAMERA DISPLAY WELDER'S HELMET

RELATED APPLICATIONS

This application claims the benefit of U.S. Provisional Application No. 61/993,476, which was filed May 15, 2014, the entire disclosures of which are incorporated herein by reference.

FIELD OF THE INVENTION

The present invention generally relates to welding safety. More particularly it relates to welder helmets having cameras and display interfaces inside the helmets.

BACKGROUND OF THE INVENTION

Arc welding is a metal fabrication process used in a multitude of industries and hobbies. While arc welding has proven itself to be a valuable process it has at least one serious drawback: in arc welding a vast amount of ultraviolet (UV) radiation is released from the arc. Such UV radiation poses a severe danger to one's eyesight.

To protect their eyesight welders use welding helmets having UV reducing glass or plastic viewing plates. By using such helmets welders can prevent injury to their face and eyes from UV radiation while preventing hot foreign materials from hitting the face. Welding helmets are so successful that government and industrial regulations mandate the use of such welding helmets.

Recent technology has provided welding helmets in which the glass quickly darkens in response to radiation from the welding arc. While this feature makes work simpler and quicker in that the welding set-up is easily visible before radiation exposure while still providing automatic UV protection when needed. Still even the most advanced prior art welding helmet does not completely reduce exposure to UV radiation. Over time a career welder can still experience deteriorating eyesight and negative effects on their skin from UV radiation. Other problems with prior art welding helmets are fogging, scratching and other factors which reduce a wearer's vision.

Another problem with arc welding and with welding in general is that many applications have critical welds that must be performed correctly. The best practice would be for such welds to be observed, verified and checked before, during, and after the actual weld. However, it is difficult or impossible for supervisors, interns, quality control personnel, contractors, government inspectors or others to view the weld set up and the actual weld.

Accordingly, there exists a need for new type of arc welding helmet that provides improved protection against eye damage and harm caused by hot objects. Ideally such arc welding helmets would provide enhanced vision capabilities both to welders and to others.

SUMMARY OF THE INVENTION

The principles of the present invention provide for a new arc welding helmet that provides improved protection against eye damage and harm caused by hot objects. Such arc welding helmets provide enhanced vision capabilities to welders and to others.

A welding helmet in accord with the present invention includes a light blocking helmet body having a shell with a head aperture that provides access into an interior cavity containing an adjustable headband. There is a viewing screen and a power source in the interior. At least one (1) camera is mounted on the shell. Electrical circuitry is operatively connected to the power source, to the viewing screen, and to the at least one camera such that the electrical circuitry causes the viewing screen to display the image produced by the at least one (1) camera.

In practice a camera mount may be used to attach the least one camera to the helmet body, beneficially at approximately the eye level of a user when the user wears the welding helmet. The camera mount may attach the at least one (1) camera to the left side of said helmet body or to the right side of the helmet body, in which case the at least one (1) camera includes an articulating stem.

The electrical circuitry beneficially includes a video processor that processes signals from the at least one camera to produce the image on the viewing screen. The electrical circuitry may further include an externally accessible control panel having a power on/off switch that is operatively connected to the power source and a manual focus adjustment for manually focusing the at least one (1) camera. That camera might include an autofocus feature but wherein the autofocus feature is overridden by the manual focus adjustment. The control panel may further include video adjustments that are operatively connected to the video processor for adjusting parameters of the viewing screen. The control panel might include a threshold adjustment that is operatively connected to video processor for setting the initial light level at the work piece for activating auto-darkening.

In practice the electrical circuitry might also include a transmitter for sending the video image produced by the at least one (!) camera to a remote receiving unit. If so, the electrical circuitry might also include a microphone in the interior and the transmitter can then send audio picked up by the microphone to the remote receiving unit. Alternatively or in addition, the electrical circuitry might include a receiver for receiving audio from the remote receiving unit and the electrical circuitry might further include a speaker in the interior for producing received audio.

There may be a second camera mounted to the helmet body and which is operatively connected to the video processor. In that case the control panel may include a camera selector switch that is operatively connected to the video processor with the camera selector switch controlling which camera produces the image.

Beneficially, the welding helmet may have an adjustable headband with a tensioning device that is adjusted by an exterior adjustment knob. The helmet body may include a plurality of ventilation apertures while a lens cover may cover the at least one (1) camera.

BRIEF DESCRIPTION OF THE DRAWINGS

The advantages and features of the present invention will become better understood with reference to the following more detailed description and claims taken in conjunction with the accompanying drawings in which like elements are identified with like symbols and in which:

Figure 1:
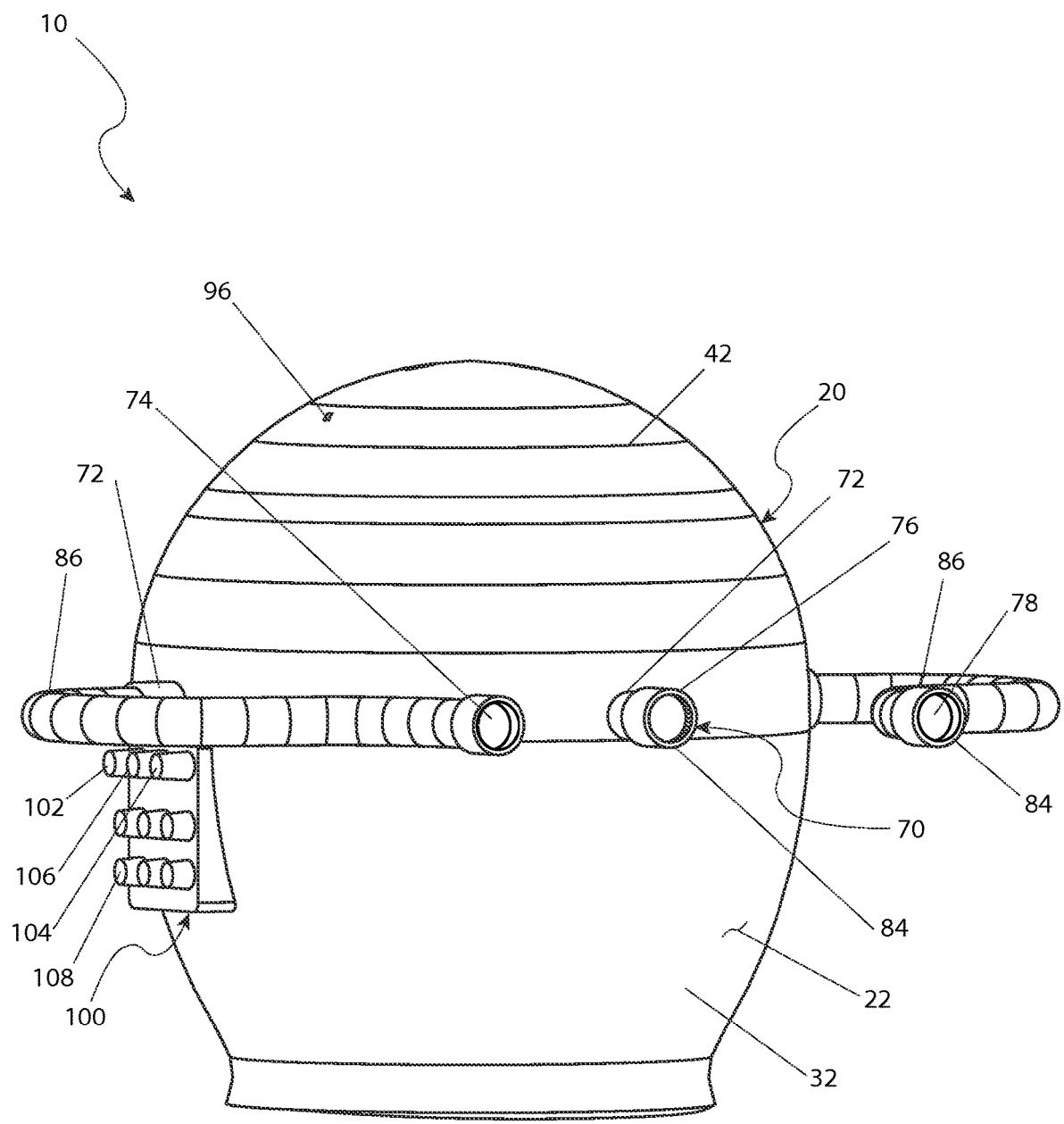
FIG. 1 is an isometric view of a welding helmet 10 that is in accord with the preferred embodiment of the present invention.

DESCRIPTIVE KEY 10 welding helmet
20 shell 22 exterior
24 interior
26 cavity
28 head aperture
32 front
34 rear
36 crown
38 slotted aperture
42 decoration
46 keeper
50 headband
52 strap
54 padding
56 insert
60 tensioning device
62 knob
64 shaft
70 video input device
72 camera mount
74 right camera
76 center camera
78 left camera
82 lens
84 protective lens cover
86 articulating stem
90 electronic circuitry
92 battery
94 battery compartment
96 charging port
100 control panel
102 on/off switch
104 camera selector switch
106 threshold switch
108 video adjustment
110 video processor
114 auto-focus
116 manual focus switch
122 viewing screen
124 image
126 transmitter
128 receiver
132 remote enable switch
134 microphone
136 speaker
140 remote receiving unit
142 transmitted wireless signal
144 received wireless signal
160 user

DETAILED DESCRIPTION OF THE PREFERRED EMBODIMENT

The preferred embodiment of the present invention is depicted within FIGS. 1 through 4. However, the invention is not limited to what is specifically illustrated and described. A person skilled in the art will appreciate that many other embodiments of the invention are possible without deviating from the basic concept of the invention. Any such work around also falls with the scope of this invention.

The terms "a" and "an" herein do not denote a limitation of quantity, but rather denote the presence of at least one (1) of the referenced items. In addition, unless otherwise denoted all directional signals such as up, down, left, right, inside, outside are taken relative to the illustration shown in FIG. 1.

Figure 3:
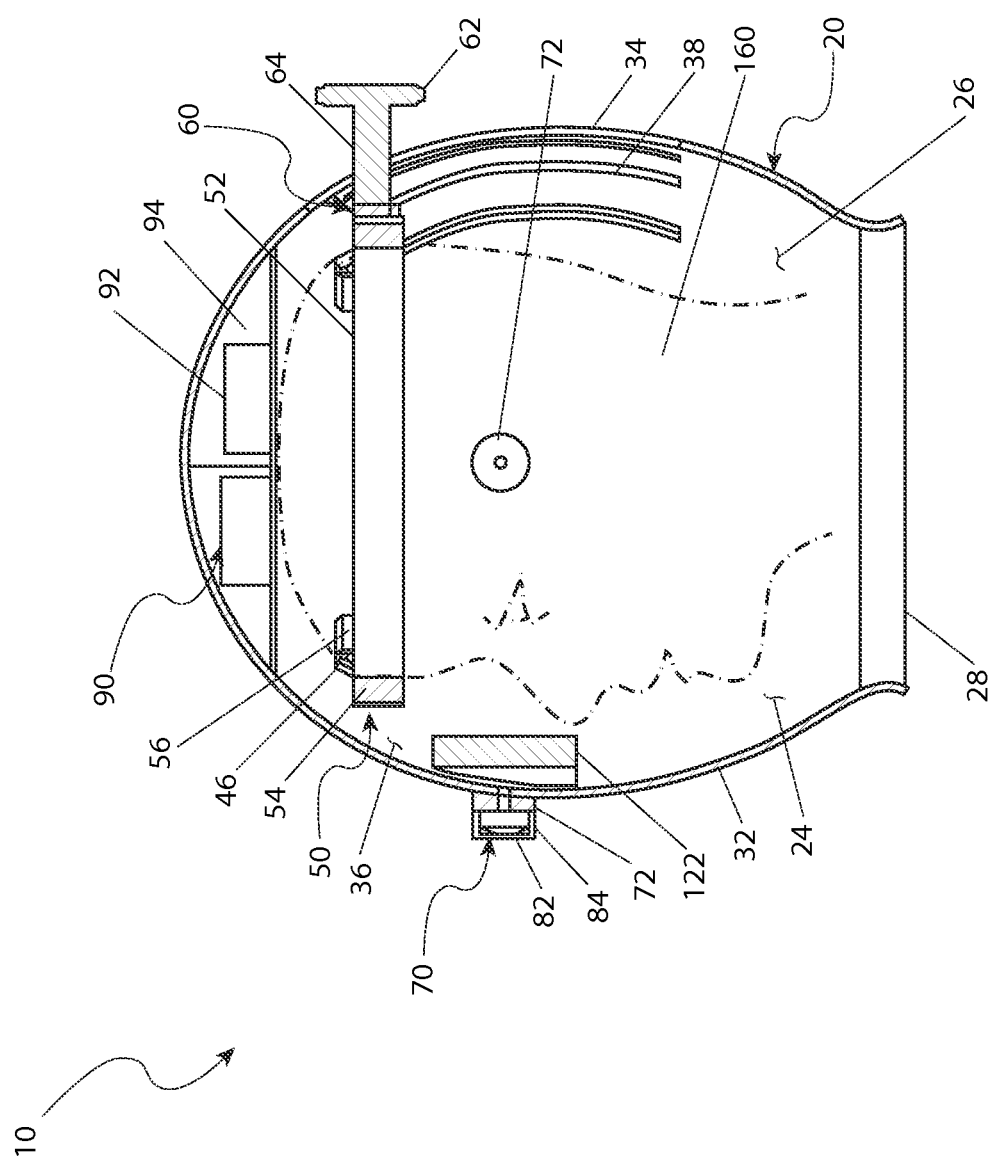
FIG. 3 is a section view along a line A-A of FIG. 2.
Figure 4:
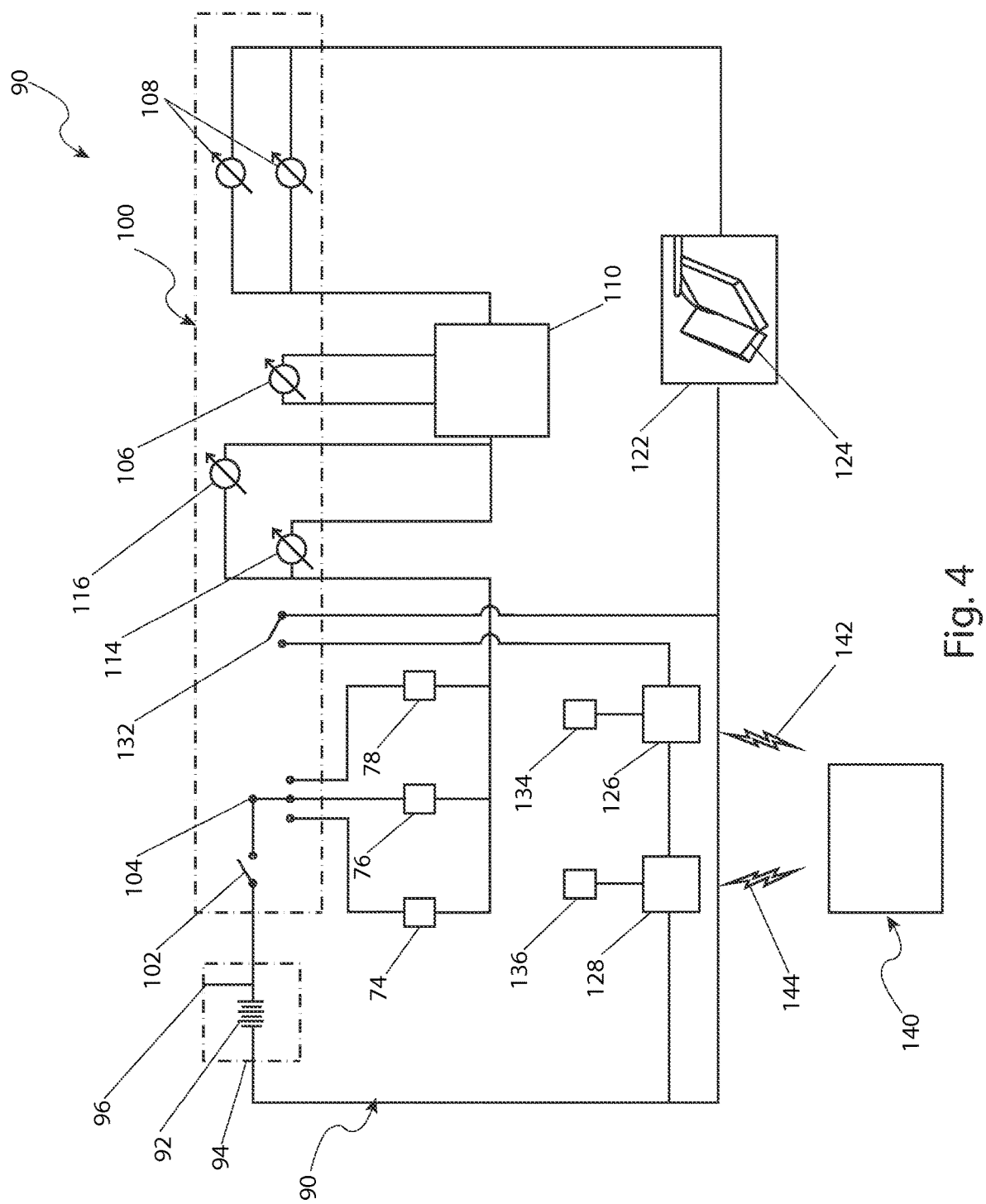
FIG. 4 is a block diagram of the electronic circuitry 90 of the welding helmet 10 shown in FIGS. 1 and 2.

Referring now primarily to FIGS. 1, 3 and 4, the present invention describes a light blocking welding helmet 10 which enables a user to perform welding operations by viewing a work piece indirectly through one (1) of a number of video input devices 70 (shown and described herein in more detail as cameras 74, 76, 78). By light blocking it is meant that the welding helmet 10 blocks all light from the front and sides and is without a transparent viewer. The cameras 74, 76, 78 are used produce a highly filtered image 124 of the welding procedure on a viewing screen 122 located within the interior 24 of a shell 20. The welding helmet 10 provides closed circuit monitoring capability that transmits at least video signals to a remote receiving unit 140. The remote receiving unit 140 can be used for quality control verification, process certification, or training.

Figure 2:
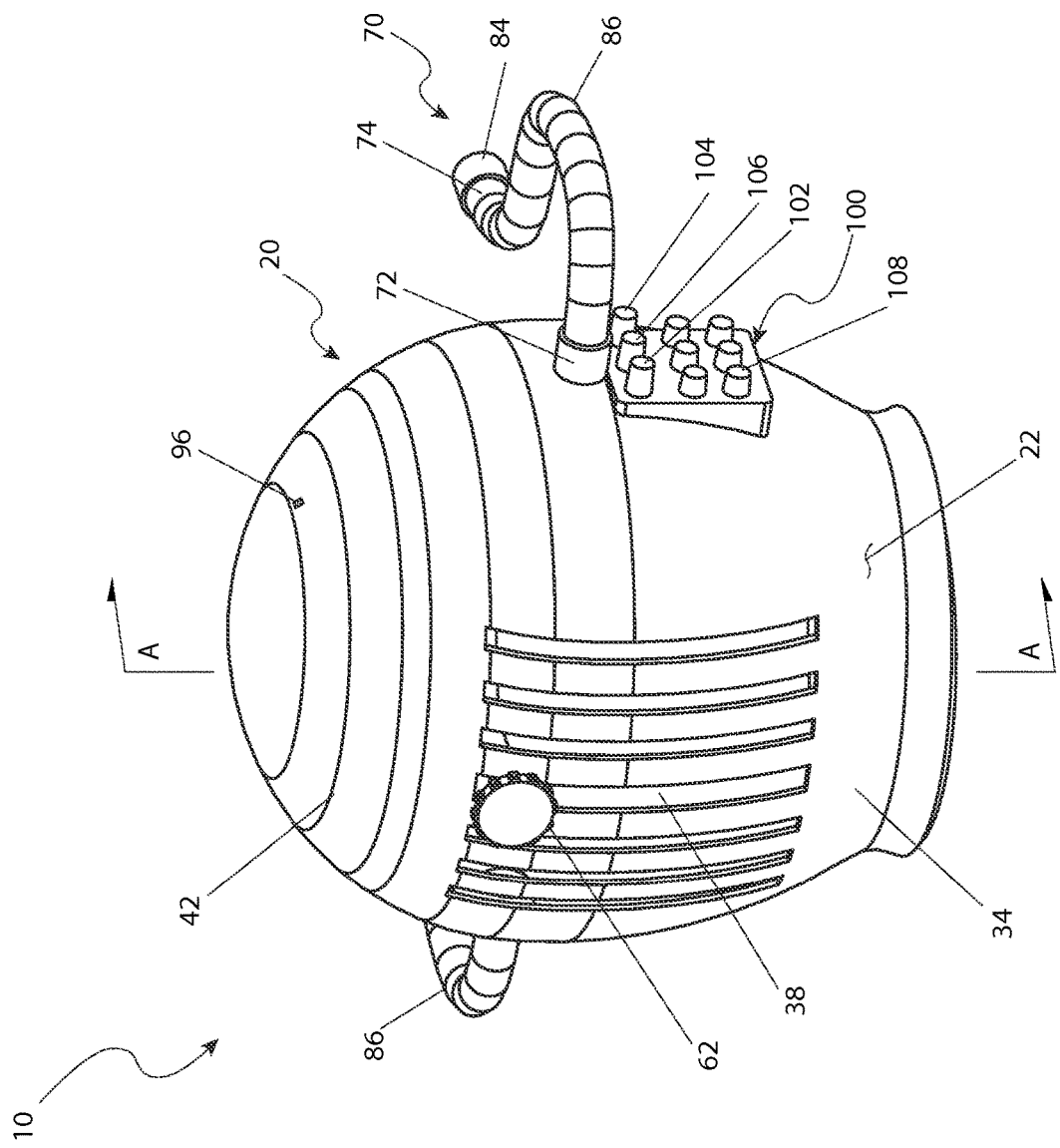
FIG. 2 is another isometric view of the welding helmet 10 shown in FIG. 1.

Referring now to FIGS. 1-3, the shell 20 has a generally quasi-spherical shape that protectively surrounds the head of a user 160 to prevent penetration of electromagnetic radiation produced by welding. The interior 24 forms a cavity 26 for the head of a user 160. At the bottom of the shell 20 is a head aperture 28 for receiving the head of a user 160 into the interior 24. The exterior 22 of the shell 20 includes a control panel 100 and camera mounts 72. The camera mounts 72 hold cameras 74, 76, 78 which are usually directed toward the front 32 of the welding helmet 10. At the rear 34 of the shell 20 are slotted apertures 38 for providing ventilation of the interior 24. The apertures 38 permit free exchange of air to provide comfort for the user 160.

While the camera mounts 72 may be located anywhere on the exterior 22 one preferential location of a camera mount 72 and its center camera 76 is centrally located on the front 32 approximately near the location of the eyes of the user 160, best illustrated in FIG. 3. By approximate it is meant that the location of the center camera 76 provides the user with a display (discussed in more detail subsequently) having a field of view that corresponds with the line of sight of a user 160, thus presenting the user with a familiar orientation. The center camera 76 is preferably rigidly fixed to maintain the constancy of that configuration and thus a consistent orientation. A right camera 74 is preferably mounted on an articulating stem 86 attached to a camera mount 72 on the right side of the shell 20. A left camera 78 is attached to another articulating stem 86 attached to a camera mount 72 on the left side of the shell 20.

The articulating stems 86 are interconnected, segmented, tubular structures used to support a camera 74, 78 in a spatially adjustable configuration relative to the shell 20. Any necessary wiring associated with a camera 74, 78 or the transmission of a video signal from a camera 74, 78 to any signal conditioning equipment is routed through the articulating stem 86 and the camera mount 72 it is attached to.

The cameras 74, 76, 78 can be any of a variety of commercially available, low voltage, optical capturing devices which output digitized data. The digitized data is applied to a video processor 110 for subsequently processing. The cameras 74, 76, and 78 are electrically powered by a battery 92 in a battery compartment 94 in the interior 24. Power is applied through an on/off switch 102 and through a camera selector switch 104 of the control panel 100. Each camera 74, 76, and 78 is equipped with a lens 82 having a replaceable protective lens cover 84. Each lens 82 can be variably focused on the work area either by an auto-focus 114 or by a manual focus adjustment 116 on the control panel 100. The protective lens cover 84 is a sacrificial device attached to the lens 82 by any convenient means such as threads or a friction fit.

Refer now to FIG. 3 for a section view taken along line A-A of as seen in FIG. 2. The welding helmet 10 is retained on the head of a user 160 by an adjustable headband 50. The adjustable headband 50 is held in place in the interior 24 of the shell 20 by keepers 46 which project from the crown 36 of the shell 20. The keepers 46 accept and retain the strap 52 of the headband 50. The strap 52 is preferably a thermoplastic band that encircles the head of a user 160 about the temples. The strap 52 includes a tensioning device 60 for adjusting the size of the headband 50. Padding 54 is added to the interior of the strap 52 to provide comfort to the user 160. The padding 54 is preferably foamed urethane attached to the strap 52 by an adhesive. As is common in many helmets the tensioning device 60 may be a toothed or otherwise indexed mechanism adjustable by turning an adjustment knob 62 that extends through the shell 20 so as to be readily accessible by the user 160.

Still referring to FIG. 3, disposed at the front 32 of the interior 22 of the shell 20 is the viewing screen 122. The viewing screen 122 is a video output device that is preferably located in the direct field of vision of a user 160. The viewing screen produces an image 124 of what is captured by the selected camera 74, 76, or 78.

Turning now mostly to FIGS. 1 and 4, the control panel 100 has video adjustments 108 that adjust the parameters of the interior viewing screen 122, such as tint, brightness, and contrast, and other parameters of the video processor 110. Also included is a threshold adjustment 106 that enables a user 160 to set the initial light level at the work piece for activating the auto-darkening feature of the video processor 110. The specific arrangement of the video adjustments 108, the on/off switch 102, and the camera selection switch 104 may be varied according to the operating parameters incorporated into the video processor 110.

As shown the control panel 100 is attached to the exterior 22 of the shell 20 in a location convenient for the easy manipulation of the various controls 102, 104, 106, and 108. The location of the control panel 100 could also be influenced by a preferential hand usage of the user 160 without limiting the scope of the welding helmet 10. It would not be unreasonable to favor a location in which either the right camera 74 or the left camera 78 could be positioned to view the control panel 100 such that manipulation of the control panel 100 could be performed by the user 160 without removing the welding helmet 10.

The shell 20 is preferably composed of metal with a protective coating or plating to inhibit pitting which might result from impingement of globules of molten metal and deleterious effects of the environment. Additionally, it is envisioned that some surface portions of the exterior 22 of the shell 20 may be provided with any of various decorations 42 which may include script, images, or logos based upon the preference of a user 160 and having symbols, lines, pictures, and the like, in various colors and patterns, to further customize and personalize the welding helmet 10.

Refer now to FIG. 4 for a block diagram of the electronic circuitry 90 of the welding helmet 10. The electronic circuitry 90 includes a rechargeable battery 92 which powers the welding helmet 10. The battery compartment 94 within the shell 20 is equipped with a charging port 96 for recharging the battery 92. The video processor 110 is located in the electronic circuitry 90. The camera selector switch 104 on the control panel 100 connects to the video processor 110 and selects the right camera 74, the center camera 76, or the left camera 78 to be used for viewing the work pieces. Initially the focus of the selected camera 74, 76, or 78 is automatically set by a proximity type auto-focus switch 114. However, the auto-focus switch 114 can be overridden by a manual focus 116 if the need arises.

The control panel 100 is equipped with a remote enable switch 132 which activates a transmitter 126 to send the video image via wireless signals 142 to a remote receiving unit 140 for monitoring, recording, or analysis by an individual other than the user 160. A microphone 134 within the shell 20 enables commentary from the user 160. Conversely a receiver 128 within the shell 20 operates a speaker 136 to enable verbal instructions to be communicated to the user 160 via received wireless signals 144.

The preferred embodiment of the present invention can be utilized in a simple and straightforward manner with little or no training After initial purchase or acquisition of the welding helmet 10 it would be installed as indicated in FIG. 3. The method of installing and utilizing the welding helmet 10 may be achieved by performing the following steps: acquiring a model of the welding helmet 10 having a desired size and style to suit the taste of a user 160; installing a fully charged battery 92 into the battery compartment 94; adjusting the on/off switch 102 on the control panel 100 to the "ON" position; adjusting the camera selector switch 104 to the center camera 76; adjusting the video variables switch 108 to a level of tint, contrast, and brightness of the image 124 on the viewing screen 122 acceptable to the user 160; adjusting the threshold switch 106 to automatically darken an image 124 at an illumination level slightly higher than the ambient light level on the work piece; donning the welding helmet 10; adjusting the headband 50 by manipulating the knob 62 of the tensioning device 60; welding the work pieces in a normal manner while monitoring the image 124 on the viewing screen 122. The angle or perspective of the work area can be modified for improved visibility by changing the camera selector switch 104 to view an image 124 from the right camera 74 or from the left camera 78. The battery 92 can be recharged within the battery compartment 94 by the simple connection of an appropriate charging circuit to the charging port 96.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A welding helmet, comprising:
   a helmet body comprising a shell configured to completely surround a head of a wearer and that is permanently opaque to light, a head aperture disposed through a lower end of said shell to provide access to an interior cavity, and an adjustable headband coupled within said interior cavity to engage said head of said wearer;
   at least one camera mount connected to an exterior of said shell;
   at least one articulating stem connected to and extending outwardly from said at least one camera mount;
   at least one camera connected to a free end of said at least one articulating stem and configured to generate a live digital video of a field of view, wherein said at least one articulating stem adjusts a position and orientation of said at least one camera;

a digital viewing screen mounted to said shell within said interior cavity of said helmet body and communicatively coupled to said at least one camera to display said live digital video generated by said at least one camera;

a control panel mounted to said exterior of said shell and operatively coupled to said at least one camera and said digital viewing screen, wherein said control panel comprises a plurality of digital video adjustment controls to adjust digital video parameters of said live digital video displayed by said digital viewing screen;

electrical circuitry operatively connected to said digital viewing screen, said at least one camera, and said control panel, wherein said electrical circuitry causes said digital viewing screen to display said live digital video produced by said at least one camera; and, a power source disposed within said interior cavity of said helmet body and electrically coupled to said at least one camera, said digital viewing screen, said control panel, and said electrical circuitry.

2. The welding helmet of claim 1, wherein a center camera mount is connected to a front of said exterior of said shell, and a center camera is fixed to said center camera mount with such that said field of view is at approximately eye level of said wearer.

3. The welding helmet of claim 1, wherein a left camera mount is connected to a left side of said exterior of said shell, a left articulating stem is connected to said left camera mount, and a left camera is connected to said left articulating stem, wherein said left articulating stem adjusts said position and orientation of said left camera.

4. The welding helmet of claim 1, wherein a right camera mount is connected to a right side of said exterior of said shell, a right articulating stem is connected to said left camera mount, and a right camera is connected to said left articulating stem, wherein said right articulating stem adjusts said position and orientation of said right camera.

5. The welding helmet of claim 1, wherein said electrical circuitry comprises a video processor, wherein said at least one camera transmits digital video signals to said video processor, wherein said video processor processes said digital video signals and generates said digital video, wherein said digital video adjustment controls are operatively coupled to said video processor to adjust said digital video parameters of said digital video, and wherein said video processor transmits said digital video for display on said digital viewing screen.

6. The welding helmet of claim 5, wherein said control panel further comprises a power on/off switch operatively connected to said power source and a manual focus adjustment operatively coupled to said at least one camera for manually focusing said at least one camera.

7. The welding helmet of claim 6, wherein said electrical circuitry further comprises an autofocus feature for autofocusing said at least one camera, and wherein said autofocus feature is overridden by said manual focus adjustment control.

8. The welding helmet of claim 5, wherein said digital video parameters controlled by said digital video adjustment controls comprise tint, brightness, and contrast.

9. The welding helmet of claim 5, wherein said control panel further comprises a threshold adjustment control operatively connected to said video processor to set an initial light level for activating auto-darkening.

10. The welding helmet of claim 1, wherein said electrical circuitry further comprises a transmitter for transmitting said live digital video produced by said at least one camera to a remote receiving unit.

11. The welding helmet of claim 10, wherein said remote receiving unit displays said live digital video.

12. The welding helmet of claim 10, wherein said electrical circuitry further comprises a microphone mounted to said shell within said interior cavity, and wherein said transmitter transmits audio picked up by said microphone to said remote receiving unit.

13. The welding helmet of claim 10, wherein said electrical circuitry further comprises a receiver for receiving audio from said remote receiving unit, and wherein said electrical circuitry further comprises a speaker mounted to said shell within said interior cavity for reproducing received audio.

14. The welding helmet of claim 1, further comprising at least one other camera mounted to said exterior of said shell and operatively connected to said electrical circuitry.

15. The welding helmet of claim 14, wherein said control panel further comprises a camera selector switch to control which of said at least one camera and said at least one other camera produces said live digital video.

16. The welding helmet of claim 1, wherein said digital viewing screen is located in a direct field of vision of said wearer.

17. The welding helmet of claim 1, wherein said adjustable headband comprises a tensioning device, and an exterior adjustment knob coupled to said tensioning device to adjust a size of said adjustable headband.

18. The welding helmet of claim 1, wherein said helmet body further comprises a plurality of ventilation apertures disposed through said shell.

19. The welding helmet of claim 1, further comprising at least one lens cover removably coupled over said at least one camera.

20. The welding helmet of claim 1, wherein:
said at least one camera mount comprises:
a center camera mount connected to a front of said exterior of said shell;
a left camera mount connected to a left side of said exterior of said shell; and
a right camera mount connected to a right side of said exterior of said shell;
said at least one articulating stem comprises:
a left articulating stem connected to said left camera mount; and
a right articulating stem connected to said right camera mount;
said at least one camera comprises:
a center camera fixed to said center camera mount;
a left camera connected to said left articulating stem, said left articulating stem adjusts said position and orientation of said left camera; and
a right camera connected to said right articulating stem, said right articulating stem adjusts said position and orientation of said right camera, and
said control panel further comprises a camera selector switch to control which one of said center camera, said left camera, and said right camera produces said live digital video for display by the digital viewing screen.

* * * * *